United States Patent
Bansal

(10) Patent No.: US 10,711,056 B2
(45) Date of Patent: Jul. 14, 2020

(54) AGLYCOSYLATED ANTI-PROPERDIN ANTIBODIES

(71) Applicant: NovelMed Therapeutics, Inc., Cleveland, OH (US)

(72) Inventor: Rekha Bansal, Twinsburg, OH (US)

(73) Assignee: NOVELMED THERAPEUTICS, INC., Cleveland, OH (US)

( * ) Notice: Subject to any disclaimer, the term of this patent is extended or adjusted under 35 U.S.C. 154(b) by 511 days.

(21) Appl. No.: 14/369,370

(22) PCT Filed: Dec. 28, 2012

(86) PCT No.: PCT/US2012/072142
§ 371 (c)(1),
(2) Date: Jun. 27, 2014

(87) PCT Pub. No.: WO2013/102123
PCT Pub. Date: Jul. 4, 2013

(65) Prior Publication Data
US 2015/0291686 A1    Oct. 15, 2015

Related U.S. Application Data

(60) Provisional application No. 61/581,080, filed on Dec. 28, 2011.

(51) Int. Cl.
*A61K 39/395* (2006.01)
*C07K 16/18* (2006.01)

(52) U.S. Cl.
CPC .......... *C07K 16/18* (2013.01); *C07K 2317/41* (2013.01); *C07K 2317/51* (2013.01); *C07K 2317/52* (2013.01); *C07K 2317/64* (2013.01); *C07K 2317/71* (2013.01); *C07K 2317/92* (2013.01)

(58) Field of Classification Search
None
See application file for complete search history.

(56) References Cited

U.S. PATENT DOCUMENTS

| 2007/0041972 | A1 | 2/2007 | Rother et al. | |
|---|---|---|---|---|
| 2007/0048300 | A1* | 3/2007 | Taylor | A61K 47/48215 424/133.1 |
| 2008/0124278 | A1 | 5/2008 | Taylor et al. | |
| 2009/0041770 | A1* | 2/2009 | Chamberlain | C07K 16/082 424/134.1 |
| 2010/0111946 | A1* | 5/2010 | Bansal | A61K 38/1725 424/133.1 |
| 2010/0203056 | A1* | 8/2010 | Irving | A61K 31/7068 424/139.1 |
| 2010/0261248 | A1* | 10/2010 | Kim | A61K 47/48415 435/188 |
| 2011/0212087 | A1* | 9/2011 | Strohl | C07K 16/00 424/133.1 |
| 2012/0100140 | A1* | 4/2012 | Reyes | C07K 16/00 424/134.1 |

FOREIGN PATENT DOCUMENTS

| EP | 0307434 B1 | 9/1993 |
|---|---|---|
| JP | 2007501021 A | 1/2007 |
| JP | 2008500012 A | 1/2008 |
| WO | WO-2005/007809 A2 | 1/2005 |
| WO | WO 2009/110918 * | 9/2009 |

OTHER PUBLICATIONS

Jefferis, Nature Reviews / Drug Discovery 8: 226-234, Mar. 2009.*
Beck et al., "Therapeutic antibodies and related products: choosing the right structure for success," Med Sci (Paris). 25(12):1024-1032 (2009) (English language abstract provided) (11 pages).
Labrijn et al., "When binding is enough: nonactivating antibody formats," Curr Opin Immunol. 20(4):479-485 (2008).
Natsume et al., "Engineered antibodies of IgG1/IgG3 mixed isotype with enhanced cytotoxic activities," Cancer Res. 68(10):3863-72 (2008).
Salfeld, "Isotype selection in antibody engineering," Nat Biotechnol. 25(12):1369-72 (2007).

* cited by examiner

*Primary Examiner* — Phillip Gambel
(74) *Attorney, Agent, or Firm* — Tarolli, Sundheim, Covell & Tummino LLP

(57) ABSTRACT

The invention is a method for reducing the effector functions of a therapeutic neutralizing antibody by administering to the afflicted subject an effective amount of an engineered aglycosylated human monoclonal antibody containing an engineered Fc region, wherein aglycosylation of the Fc region prevents therapeutic antibody-mediated cell activation, inflammation, C1q binding to the antibody and antibody triggered classical pathway activation.

7 Claims, 17 Drawing Sheets
**Specification includes a Sequence Listing.

FIGURE 1

| PROPERTY | IgG1 | IgG2 | IgG4 |
|---|---|---|---|
| Normal Properties | | | |
| Structural Stability | +++ | +++ | +/- |
| Serum Half-life, T1/2 (days) | ~23 | ~23 | ~23 |
| Serum Concentration (mg/mL) | 9 | 3 | 0.5 |
| Complement Activation | | | |
| Classical Pathway | ++ | + | - |
| Alternative Pathway | - | + | - |
| ADCC | +++ | +/- | +/- |
| Fc Receptor Binding | | | |
| FcγRI (CD64) high affinity – $1 \times 10^{-9}$ M | +++ | + | + |
| FcγRIIa/b (CD32) low affinity – $5 \times 10^{-5}$ M | ++ | +/- | +/- |
| FcγRIIIa/b (CD16) low affinity – $2 \times 10^{-6}$ M | ++ | +/- | + |

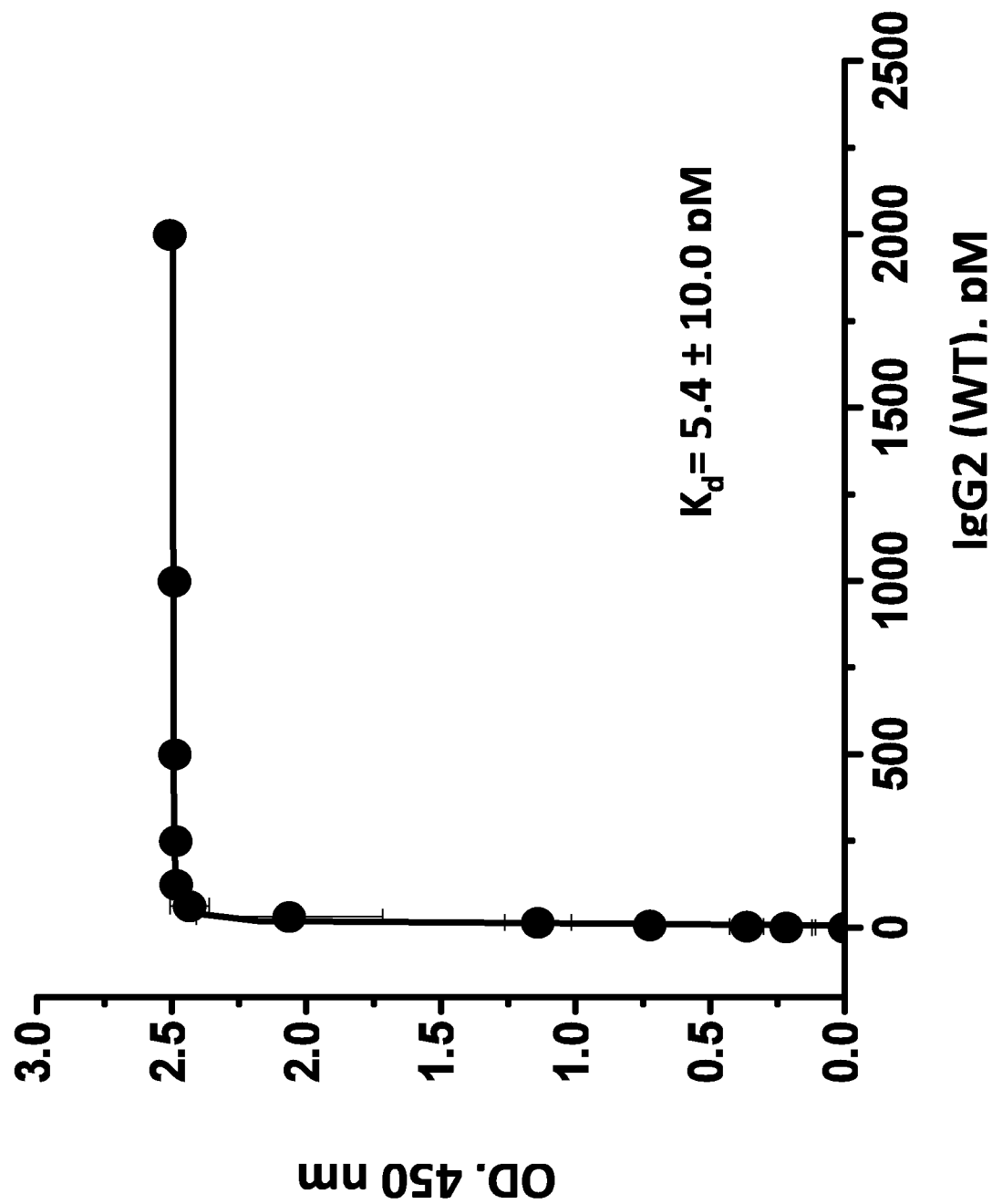

AGLYCOSYLATED ANTI-PROPERDIN ANTIBODIES

RELATED APPLICATIONS

This application claims benefit of 61/581,080, filed Dec. 28, 2011, the subject matter of which is incorporated herein by reference in its entirety.

GOVERNMENT FUNDING

This invention was made with government support under Grant No. RHL099015 awarded by The National Institutes of Health. The United States government has certain rights to the invention.

BACKGROUND

Immmunoglobulins (IgGs) are large molecules. They are antibodies composed of two heavy chains and two light chains. Each light chain has two portions; a constant region (LC) and a variable region (LV). Each heavy chain has one variable portion (HV) and four constant portions (CH1, CH2, CH3 and CH4). Each variable portion on each chain is followed by a constant portion. Each light chain is linked to a heavy chain by one or more covalent interchain disulfide bond(s). Each heavy and light chain also contains regularly spaced intra-chain disulfide bridges. The variable domains are composed of complementarity determining regions (CDRs) and framework regions (FWs) that are specific to each antibody. The variable domains determine the function and binding of the antibody. CDRs are the primary binding segments of the antibody involved in antigen binding. The constant domain, composed of the CH1, CH2, and CH3 regions, is not involved in antigen binding. The CH2 and CH3 constitute the Fc region of the antibody. The Fc region is responsible for several "effector functions" (see below), including certain biological activities which can be unfavorable in the context of therapeutic neutralizing antibodies. Such unfavorable effector functions include C1q binding and antibody-dependent cellular cytotoxicity (ADCC) response. The Fc region of an antibody, specifically the effector domain, binds to Fc receptors (Fc.gamma.Rs) on the surface of immune effector cells such as macrophages. This leads to the phagocytosis or lysis of the targeted cells. In complement-dependent cytotoxicity (CDC), the antibodies kill the targeted cells by triggering the complement cascade, and resulting MAC formation, at the cell surface.

There are five major classes of immune-globulins: IgA, IgD, IgE, IgG and IgM. The IgG(s) are further divided into four isotypes: IgG1, IgG2, IgG3, and IgG4. These isotypes elicit differential responses due to the sequences located within the constant domains. The IgG1, IgG2, and IgG3 isotypes are known to cause complement system activation and CDC. (See FIG. 1). The IgG1 and IgG3 isotypes are known to mediate ADCC. The four IgG isotypes vary in the compositions of their heavy chains. Among therapeutic antibodies, human IgG1 is the most commonly used isotype. Accordingly, attempts to modify therapeutic antibody effector functions have been focused on IgG1 isotypes. However, different IgG isotypes, with different inherent effector function properties, are often more useful in the context of reducing and/or exploiting effector functions. There is a need in the art to develop the use of the IgG2, IgG3, IgG4 isotypes, and isotype hybrids, with and without Fc modifications, for use as therapeutic antibodies. The present invention aims to address some of these needs.

Hybrid Isotypes—The hinge region of the IgG antibody is located between the CH1 and CH2 portions of the heavy chain, and is particularly susceptible to proteolytic cleavage. Antibodies can be recombinantly engineered to form hybrid isotypes which contain portions from two or more different isotypes. For example, the prior art includes a hybrid antibody which contains the variable portion and the first constant portion of an IgG2 isotype antibody fused to the CH2, and CH3 portions of an IgG4 isotype antibody. (US Patent Application 20070041972).

Fc Mediated Effector Functions—The Fc "effector functions" are the biological activities of an antibody (be it a natural antibody or an engineered antibody) other than the antibody's primary function and purpose. In the case of therapeutic neutralizing antibodies, the effector functions are the biological activities of the antibody other than the neutralization of the target protein or pathway. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); lack of activation of platelets that express Fc receptor; and B cell activation. Many effector functions begin with Fc binding to an Fc gamma receptor (Fc.gamma.R). There are three subclasses of Fc.gamma.R: Fc.gamma.RI (CD64), Fc.gamma.RII (CD32) and Fc.gamma.RIII (CD16).

SUMMARY

The invention is for engineered antibodies containing Fc variants, derived from parent antibodies of isotypes IgG2, IgG3, and IgG4, in which at least one amino acid in the Fc region has been modified. Most therapeutic antibodies are IgG isotypes, which tend to display more effector function activity. Even unmodified wild type isotypes IgG2, IgG3, and IgG4 exhibit less effector function activity than do antibodies of IgG1 isotype. The Fc region of the antibody is the locus of various undesirable effector functions, such as classical pathway activation and antibody mediated cell lysis. The difference in effector function activity between isotype IgG1 and other isotypes is attributable to the differences in the Fc regions of the isotypes. In various embodiments of the invention, the Fc region is derived from an antibody of an isotype other than IgG1. The invention is a method for reducing the effector functions of a therapeutic neutralizing antibody by administering to the afflicted subject an effective amount of an engineered human monoclonal antibody, of an isotype other than IgG1, wherein modification of the Fc region prevents antibody-mediated cell activation, C1q binding, inflammation and antibody triggered classical pathway activation. The invention describes engineered antibodies and antibody hybrids which have mutations within the Fc region, and/or Fc regions derived from isotypes other than IgG1. Antibodies which are hybrids with variable target binding regions derived from one isotype, joined with modified and/or unmodified Fc regions derived from an IgG2, IgG3 or IgG4 isotype, are contained in this invention. The purpose of the invention is to enable use of therapeutic neutralizing antibodies with reduced Fc mediated responses, but with normal in vivo half lives.

In some applications, such as in the use of therapeutic antibodies as anti-cancer drugs, certain effector functions are desirable. In other applications, certain effector functions are undesirable. For example, in the case of therapeutic antibodies which target the alternative pathway specific proteins, effector functions which activate the classical complement pathway are not desirable. In order to minimize or eliminate undesirable side effects of a therapeutic antibody, the invention provides a method for minimizing or eliminating effector functions.

Role of the Fc Region—The Fc region of an antibody mediates the antibody's effector functions and serum half life. These effector functions include, but are not limited to; complement-dependent cytotoxicity (CDC), antibody-dependent cellular cytotoxicity (ADCC), antibody-dependent cell phagocytosis (ADCP), and C1q dependent classical pathway activation. The binding of IgG(s) to an Fc.gamma.R and/or C1q is governed by specific residues or domains within the Fc regions. Binding also depends on residues located within the hinge region and within the CH2 portion of the antibody. Numerous mutations have been made by several inventors to identify regions involved in Fc binding. Engineering the Fc region of a therapeutic monoclonal antibody (mAb), or Fc fusion protein, enables one to generate molecules that are better suited to the pharmacology activity required of neutralizing therapeutics.

FcRn: One type of Fc receptor is the neonatal Fc receptor (FcRn). This receptor is crucial in determining the serum half-life of monoclonal antibodies. FcRn is expressed on the surface of endothelial cells and binds to IgGs in a pH-dependent manner. The binding results in the antibodies becoming internalized into endocytic vesicles. This enables the cells to recycle the antibodies back into the serum, contributing to the IgG half-life of approximately 23 days.

Fc Effector & C1q Binding: Effector functions of the antibody are important in vivo and have been exploited for their advantages in the development of anti-cancer therapeutic antibodies. Although enhanced effector functions are required for developing anti-cancer therapeutics, reduced effector functions are necessary in the development of neutralizing antibodies for chronic indications. All four IgG isotypes bind and activate Fc receptors Fc.gamma.RI, Fc.gamma.RIIA, and Fc.gamma.RIIIA Since Fc.gamma.RIIB is an inhibitory receptor, antibody binding to this receptor does not activate complement and cellular responses. Fc.gamma.RI is a high affinity receptor that binds to IgG in monomeric form. Fc.gamma.RIIA and Fc.gamma.RIIIA are low affinity receptors that bind IgG only in multimeric form and have slightly lower affinity. Thus large amounts of an IgG antibody would be needed to generate an immunogenic response.

By "wild type or WT" herein is meant an amino acid sequence or a nucleotide sequence that is found in nature, including allelic variations. A WT protein has an amino acid sequence or a nucleotide sequence that has not been intentionally modified.

Aglycosylation—It is known that aglycosylation of the Fc region of an IgG antibody will disrupt the effector functions of the antibody. Aglycosylation of the Fc region can be accomplished in a variety of ways. One such way is via mutation of the amino acid (asparagine) at location 297 within the CH2 portion of the Fc region. There appears to be a single conserved site at asparagine 297 in IgG1, IgG2, IgG3, and IgG4. The sugar chain attached to this glycosylation site is important for IgG effector functions. Crystallography studies have demonstrated that the carbohydrate chains form a bridge between the two opposing CH2 domains. Aglycosylated IgG no longer binds to FcγRs or to C1q, and thus, does not trigger ADCC and classical complement pathway activation.

Numerous reports have shown that modulation of IgG bound to FcγRIIIA is important for generating therapeutic mAbs for tumor suppression. Therapeutic mAbs require the presence of activated FcγR to control tumor progression and to increase survival rates in mouse models. Thus, strategies to modify the glycosylation profile of human IgG1 have been extensively explored in the context of anti-cancer therapeutics. Fc receptors (FcγRs) link the cellular and humoral immune responses. The stimulation of cells expressing these receptors by the Fc regions of IgGs has dramatic consequences, including ADCC, ADCP, classical pathway activation, oxidative burst, and release of inflammatory mediators. IgG1 has a strong effect on classical pathway activation and Fc effector function. The removal of glycosylation in the Fc region of the IgG1 isotype greatly reduces classical pathway activation. Fc mediated effector functions can be reduced by introducing selected point mutations within the Fc region. As will be discussed in the detailed description of the invention, reduction of Fc mediated effector functions can also be achieved by substituting the Fc region of the IgG1 isotype with the Fc region of another isotype.

In one embodiment of the present invention, the engineered antibody contains a mutation at position 297 which prevents glycosylation at the site. The asparagine at position 297 can be replaced with amino acid residues that do not result in N-linked glycosylation. Some of these amino acids can be identified as Alanine and glutamic acid. Preventing glycosylation prevents undesired effector functions.

Prior Art Methods for Preventing C1q Binding & Complement Activation—C1q forms the C1 complex with C1r and C1s, the first component of the complement-dependent cytotoxicity (CDC) pathway. Effector functions are inherent properties of full length IgG(s) and must be down-regulated/inhibited in the context of therapeutic monoclonal antibodies which neutralize specific proteins. Within the prior art are three different strategies for reducing antibody effector functions: 1) mutation of amino acids, located within the Fc domain, that are involved in the effector binding interactions, 2) removal of Fc region and replacement of the Fc region with Poly Ethylene Glycol (PEG) conjugates, and 3) replacing the Fc region of an IgG2 antibody with that of an IgG4 antibody (creating a hybrid isotype). In vitro assays have been used to demonstrate the binding of C1q to the antibodies.

Aglycosylation via Point Mutation at N297—It has been shown that glycosylation induces classical pathway activation which leads to the formation of inflammatory mediators including C3a, C5a, C5b-9, and a series of harmful interleukins including IL-1, TNF-alpha. This unwanted activation of the classical complement pathway can be reduced by mutating the asparagine (N) at position 297 to either Alanine (A) or glutamine (Q). An aglycosylated IgG1 antibody has reduced C1q binding (shown in Table 1). Such aglycosyl antibodies can also be generated by utilizing enzymatic and/or chemical de-glycosylation. The host cells may be bacterial, mammalian viral, or yeast. Aglycosyl antibodies or antibody derivatives are produced in transgenic mammals that express the antibody in milk, in order to facilitate large scale production of aglycosyl antibodies. Nearly all marketed antibodies are IgG1.

Aglycosylation via PEG Substitution—Replacement of the Fc region with Poly Ethylene Glycol (PEG) conjugates reduces effector functions, but also reduces the half life of the antibody. Therefore, this method is not ideal in the context of therapeutic antibodies with more chronic indications.

Aglycosylation via Isotype Hybrids—IgG2 and IgG4 antibodies, although glycosylated, inherently have reduced complement activation and reduced Fc binding (see Table 1). These observations suggest that these isotypes contain Fc regions with amino acid sequences or protein motifs which demonstrate reduced Fc effector functions and complement dependent cytotoxicity. In order to further reduce the effector functions of these isotypes, aglycosylating mutations have been introduced into the Fc region of IgG2 antibodies, as have been introduced into IgG2m4 and IgG2m3 antibodies. These antibodies demonstrate even further reduced effector functions. Positions 234/235/237 appear to be critical in mediating the Fc response and therefore have been mutated from V/A/G to A/A/A. Other mutations such as 330/331 also appear to be important and extensively studied by numerous groups.

In one embodiment, the newly generated antibody of the present invention will have intact FcRn binding and a retained half life. An antibody with reduced effector functions and reduced C1q binding ability is one which has reduced binding affinity to Fc receptors I, II, and III and has reduced ADCC, CDC, and C1q binding compared to the non-mutant, native IgG. The present invention includes a method for reducing effector functions while preserving half life wherein the engineered antibody binds FcRn, but not C1q Such an antibody has a preserved half life, but does not activate the classical pathway.

As indicated, the IgG Fc region, and especially the CH2 region of the present invention can be used in the production of any non-immunostimulatory antibody or antibody-like protein, fusion protein including humanized and therapeutic antibodies, and used for preventing Fc receptor binding or binding to complement proteins. An antibody generated and produced by those skilled in the art including but is not be limited to, polyclonal or monoclonal, and chimeric or human, humanized or human neutralizing, bispecific or single chain antibodies thereof. Antibodies of the present invention can have additional moieties attached thereto such as microsphere, microparticle or pegylated molecules can be attached to the antibody or antibody fragment.

N297 Mutation to Prevent Glycosylation of IgG1—

Previous published art describes the effectiveness of the N297 mutation in preventing glycosylation and therefore decreasing the effector functions of IgG1. Compared to the IgG1, the IgG2 inherently has decreased complement pathway activation, ADCC, and Fc effector functions as shown in FIG. 1. Thus removal of glycosylation should further decrease the complement activation, ADCC activity, and Fc receptor binding. Thus the present invention targets the IgG2 isotype with a 297 mutation as IgG2 inherently has reduced effector function and complement activation. By removing glycosylation through the 297 mutation, C1q binding and effector functions can be reduced further. The mutation may include any amino acid that does not cause asparagine (asp) to become glycosylated.

Mutations within the CH2 Region of the IgG1—A series of mutations have been identified within the CH2 region of the IgG1. Published mutations encompass the entire CH2 region. It is difficult to choose the one that would give the desired decreased CDC, ADCC, and Fc receptor binding. The present invention claims the generation of antibodies with the specific CH1 deletions which reduce the CDC, ADCC, and Fc receptor (excluding the FcRn) binding. Where previous inventions involve mutations to the IgG1 isotype, the invention applies these mutations to the IgG2 isotype. These antibodies can be constructed using the CH2 deletion approach as majority of Fc effector mutations have been located within the CH2 region of the IgGs. This deletion will also generate aglycosylated antibody as N297 is a part of CH2 domain. N297 refers to asparagine at position 297 (Kabat Numbering) is replaced with Q or Ala.

IgG2 Antibody with Four IgG2m4—Previous invention has claimed the glycosylated IgG2 antibody with four mutations called IgG2m4. This mutated IgG2m4 construction was based on the IgG2 and IgG4 sequences. Some naturally found sequences from the IgG4 were incorporated in the IgG2 sequence. This mutated IgG2 appears to prevent the Fc effector functions including C1q binding and Fc receptor binding. Merk (USPTO #7700099) describes the use of a glycosylated IgG2 antibody with reduced effector function. Similar mutations to an aglycosylated IgG1 antibody would further reduce the Fc responses. The IgG2 CH1 sequences are different than the IgG1 CH1 sequences. However, it is possible to use the CH1 from IgG1, IgG3, and IgG4 and connect to Hinge, CH2 and CH3 derived from the IgG2 or IgG4 sequences. The present invention (current application) results in an antibody hybrid wherein the variable regions of an IgG1 antibody are combined with the lower constant (including Fc) regions of an IgG2 or IgG4 antibody. The CH2 domain can have mutations at one or more of the following residues 234, 235, 230, 237, 268, 297, 309, 330, and 331 (or contain no mutations) to generate an IgG1/IgG2 or IgG1/IgG4 hybrid.

BRIEF DESCRIPTION OF THE DRAWINGS

FIG. 1. Chart of characteristics of different IgG isotypes, comparing normal properties, binding, and effector function activity.

FIG. 2. Depicts binding of an IgG2 wild type (WT) to substrate-bound antigen. The antibody binds its target antigen with high affinity.

DETAILED DESCRIPTION

Definitions

Figure 3:
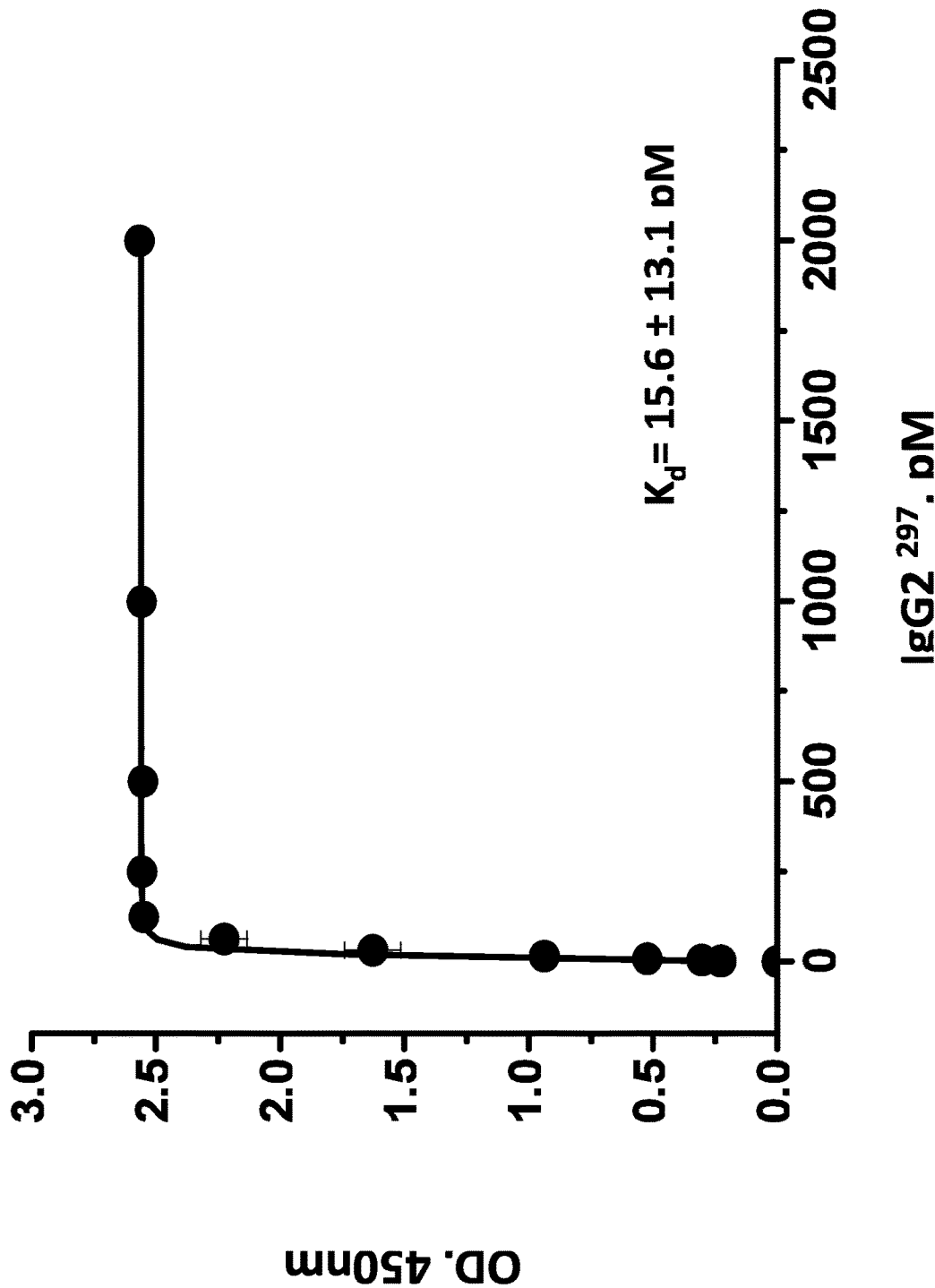
FIG. 3. Depicts binding of an aglycosylated IgG2 (297 mutation) to substrate bound antigen. The aglycosylated IgG2 antibody binds its target antigen with high affinity.

Unless specifically defined herein, all terms used in this document have the same meaning as would be understood by those of ordinary skill in the art of the present invention. The following definitions are provided for clarity, and to define their intended meaning as used in the specification and claims to describe the present invention.

"ANTIBODY DEPENDENT CELL-MEDIATED CYTOTOXICITY" ("ADCC") refers to the cell-mediated reaction wherein nonspecific cytotoxic cells expressing FcγRs recognize and cause lysis of target cells with bound antibody.

"ANTIBODY DEPENDENT CELL-MEDIATED PHAGOCYTOSIS" ("ADCP") refers to the cell-mediated reaction wherein nonspecific cytotoxic cells that express FcγRs recognize and cause phagocytosis of target cells with bound antibody.

"AGLYCOSYLATED" refers to an antibody with a hydroxyl or other functional group that is not attached to a glycosylate group. It also refers to antibodies that do not have carbohydrate residues.

As used herein, the term "ANTIBODY" refers to both antibodies and antibody fragments thereof, derived from any antibody-producing mammal (e.g., mouse, rat, rabbit, and primate including human), that specifically bind to alternative pathway specific proteins. Exemplary antibodies include monoclonal, polyclonal, recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

"ANTIBODY FRAGMENT" refers to a portion derived from or related to a full-length antibody, generally including the antigen binding or variable region thereof (see "ANTIGEN BINDING FRAGMENT"). The term "ANTIBODY FRAGMENT" refers to a portion derived from a full-length antibody, generally including the antigen binding and variable region thereof. Other antibodies include diabodies, linear antibodies, single-chain antibody molecules and multispecific antibodies formed from antibody fragments. Examples of antibody fragments include Fab, Fab', F(ab)2, F(ab')2 and Fv fragments, or scFv fragments.

"ANTIGEN BINDING FRAGMENT" (or "ANTIGEN BINDING REGION") of an antibody refers to the one or more fragments of an intact antibody that retain the ability to specifically bind to a given antigen. Antigen binding functions of an antibody can be performed by fragments of an intact antibody containing the Complementarity Determining Regions (CDRs). Examples of antigen binding fragments:

"Fab" fragments (single chain variable regions with VH and VL)

"Monovalent Fragments" (antibody fragments consisting of the VL, VH, CL and CH1 domains)

"F(ab')2" fragments (bivalent fragments comprising two Fab fragments linked by a disulfide bridge at the hinge region);

"Fd" fragments (which consist of the VH and CH1 domains of an antibody);

"Fv" fragment (which consist of the VL and VH domains of a single arm of an antibody);

single domain antibody ("dAb"), which consist of a VH domain or a VL domain;

an isolated Complementarity Determining Region ("CDR").

CDRs, as antigen binding fragments, can also be incorporated into single domain antibodies, maxi bodies, mini bodies, intrabodies, diabodies, triabodies, tetra bodies, v-NAR and bis-scFv. Antigen binding fragments of antibodies can be grafted into scaffolds based on polypeptides such as Fibronectin type III (Fn3). Antigen binding fragments can be incorporated into single chain molecules comprising a pair of tandem Fv segments (VH-CH1-VH-CH1) which, together with complementary light chain polypeptides, form a pair of antigen binding regions.

As used herein, a "SINGLE-CHAIN Fv" or "scFv" antibody fragment comprises the VH and VL domains of an antibody, wherein these domains are present in a single polypeptide chain.

"COMPLEMENT-DEPENDENT CYTOTOXICITY" ("CDC") refers to cell lysis which occurs as a result of complement system activation and MAC formation. CDC, as an effector function, is triggered by Fc binding to C1q.

"CHIMERIC ANTIBODY" is a recombinant protein that contains the variable domains and CDRs derived from an antibody of from a non-human species of animal, while the remainder of the antibody molecule is derived from a human antibody. The replacement of the non-binding region of the antibody with a human constant region enables the chimeric antibody to retain its specificity in recognizing and binding the targeted antigen while having reduced antigenicity in humans (compared to the original mouse antibody).

"CLASSICAL PATHWAY" refers to complement which is triggered by antigen-antibody complexes and requires C1Q for activation. Propagation of the classical pathway may or may not require the alternative pathway amplification loop.

"COMPLEMENTARITY DETERMINING REGIONS (CDRs)" are the key binding regions of the antibody. There are typically three CDRs found within the variable regions of each of the two heavy and light chain variable regions. CDRs can be shuffled around, in terms of location, to create a particular binding affinity. See also "ANTIGEN BINDING FRAGMENTS."

"EFFECTOR FUNCTIONS" refer to those biological activities attributable to the native Fc region of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); lack of activation of platelets that express Fc receptor; and B cell activation. In order to minimize or eliminate side effects of a therapeutic antibody, it may be preferable to minimize or eliminate effector functions.

In the context of this application "UNDESIRED EFFECTOR FUNCTIONS" include ADCC, CDC, classical pathway activation, cell activation, and antibody mediated inflammation.

An "ENGINEERED ANTIBODY" is an antibody that is not naturally produced, and which has been altered or created to achieve a specific purpose or to have a specific characteristic. For example, antibodies which have undergone deliberate modifications to their wild type forms, to have reduced effector functions, are engineered antibodies.

As used herein, the term "Fc REGION" refers to the region of the antibody that provides defense to a given antigen.

"FIRST PORTION OF THE ANTIBODY" refers to a portion of a whole antibody, a portion less than the whole, which contains the antigen binding regions of the antibody. "SECOND PORTION OF THE ANTIBODY" refers to a portion of a whole antibody, a portion less than the whole, which consists of the portion of the antibody which is not included in the first portion.

The terms "Fc receptor" or "FcγR" describe a receptor that binds to the Fc region of an IgG. "FcγRI," "FcγRII," and "FcγRIII" are subclasses of FcγRs.

As used herein, the term "REDUCED Fc EFFECTOR FUNCTION(S)" refers to the function(s) of an antibody wherein the antibody does not act against an antigen that recognizes the Fc region of the antibody. Examples of reduced Fc effector functions can include, but are not limited to, reduced Fc binding to the antigen, lack of Fc activation against an antigen, an Fc region that contains mutations to prevent normal Fc effector functions, or prevention of the activation of platelets and other cells that have Fc receptors.

"HUMAN ANTIBODY" is an antibody in which all components of the antibody are of human origin, including the framework, CDRs, and constant regions. The term "humanized" antibody is an antibody of non-human origin that retains the binding specificity of the non-human antibody while being less immunogenic in humans. See CHIMERIC ANTIBODY and HUMANIZED ANTIBODY.

As used herein, the term "IMMUNOGENICITY" refers to the ability of an antigen to initiate an immune response in a subject.

A "MODIFICATION" to an antibody, antibody fragment, and/or Fc region of an antibody, refers to a substitution, insertion, or deletion of one or more amino acids in the protein's wild type polypeptide sequence. A modified antibody, antibody fragment, and/or Fc region is one in which a modification has been artificially made.

A "PARENT ANTIBODY" is the wild type, or unmodified, antibody from which an engineered antibody, or antibody fragment, is derived.

"TARGET ANTIGEN" refers to the protein, carbohydrate, lipid, or other chemical compound to which an antibody specifically binds.

"THERAPEUTIC NEUTRALIZING ANTIBODY" refers to any antibody which has been developed to target a specific protein and is intended/anticipated to have a therapeutic effect in the subject to whom it is administered.

DETAILED DESCRIPTION OF THE INVENTION

Here we describe recombinant monoclonal therapeutic antibodies with engineered HEAVY chain constant regions that are characterized by reduced undesired effector functions, such as ADCC, CDC, classical pathway activation and antibody triggered inflammation. Our goal was to design and develop antibodies with reduced undesired effector functions. In one embodiment, the invention is an aglycosylated IgG2 isotype antibody with a modification to the amino acid at location N297. In another embodiment, the invention is an aglycosylated IgG1/IgG2 hybrid with a modified Fc region. These antibodies do not bind to C1q and therefore do not activation the classical pathway.

Literature review suggests that reduction in effector functions can be accomplished in the following three ways;

1) by producing antibodies which lacks the Fc region entirely, 2) by making mutations within the Fc region of an IgG1 isotype antibody, and 3) making a hybrid isotype antibody wherein a Fab portion from an IgG2 isotype is joined to the Fc region from an IgG4 isotype (EP1635872 A2).

Antibodies which completely lack the Fc region (method 2 above) suffer from reduced serum half life. Treatment with such an antibody would require frequent dosing in a clinic to achieve efficacy in a chronic setting. There are many clinical indications for which such frequent dosing in a clinic is impractical, if not impossible. While IgG1 antibodies with modified Fc regions do display reduced effector functions, the IgG1 isotype is not the ideal isotype for reducing effector functions. The hybrid IgG2m4 isotype antibody (method 3 above) displays some reduction in effector functions. The IgG2 and IgG4 isotypes are very similar and thus it's relatively easy to develop IgG2/IgG4 hybrids. The hybrid antibodies of the present invention demonstrate even further reduction in effector functions.

In one embodiment of the present invention, the Fc region of an IgG2 isotype is modified to produce an aglycosylated antibody with reduced effector functions. In another embodiment of the invention, the native or modified Fc region of an Ig2 or IgG3 isotype is combined with variable regions from an IgG1, IgG2, IgG3 or IgG4 isotype. The current invention is for making and using an aglycosylated antibody via site directed mutagenesis within the Fc region of an IgG2, IgG3, or IgG4 antibody, and/or recombinant engineering to produce hybrid isotypes wherein the Fc region is derived from an IgG2, IgG3, or IgG4 antibody. Such antibodies have reduced antibody dependent cell mediated cytotoxicity (ADCC), Fc gamma receptor binding and complement Dependent Cytotoxicity (CDC). Mutation within the Fc region at asparagine (N) to Alanine, and/or glutamic acid, reduces C1Q binding property of the antibody.

The current invention covers non-hybrid and hybrid antibodies with the following constructions;

1) First portion of the antibody is from an IgG1, IgG3, or IgG4 and the Fc region is from a wild type IgG4 or aglycosylated IgG4 isotype, 2) First portion of the antibody is from an IgG2 and the Fc region is from an aglycosylated IgG2, IgG3 or IgG4, 3) First of the antibody portion is from an IgG1 and the Fc region is from an unmodified IgG2, IgG3, IgG4, and 4) First portion of the antibody is from an IgG4 and the Fc portion is from an aglycosylated and glycosylated IgG1, IgG2, and IgG3

Aglycosylation of IgG1 via mutation at position 297 position within the Fc region has been described in the prior art. Such antibodies have been shown to have a longer half life in vivo. They have also been described as displaying reduced C1Q binding, reduced Fc binding, and reduced effector functions.

The terms "Fc receptor" and "FcγR" describe a receptor that binds to the Fc region of an IgG. The preferred FcγRs are the FcγRI, FcγRII, and FcγRIII subclasses. FcγRII receptors include FcγRIIA (an "activating receptor") and FcγRIIB (an "inhibiting receptor"). An isolated non-immuno-stimulatory antibody of the present invention is concomitantly incapable of binding to C1q.

In particular embodiments, the invention incorporates a substantial portion of the amino acid sequence of the Fc region of IgG2, IgG3, or IgG4. The Fc region of an immunoglobulin generally encompasses two constant domains, CH2 and CH3. As used herein, "a substantial portion of an IgG2 Fc region" is intended to mean that 80% to 98% of the amino acid sequence of the Fc region is that of native IgG2. The reduction of the ADCC, CDC, Fc binding and C1q binding is achieved by mutating the selected amino acid residues of IgG2 Fc region. The CH2 domain extends from amino acid 231 to amino acid 340. In particular embodiments, the IgG2 Fc region contains amino acid residue mutations at amino acid residues 297, 234, 235 and 331. A non-glycosylated Fc region of the aglycosylated IgG2 contains may also contain mutations at amino acid residues H268Q, V309L, A330S, and P331S in addition to the N297 mutation. The IgG2 Fc region of the present invention with mutation at 297, 234, 235, and 331 positions can be used for producing antibodies and/or fusion proteins with reduced Fc effector and C1q binding without affecting the FcRn and other pharmacologic properties of the antibody. These combinations of mutations can also be introduced into polyclonal or monoclonal antibodies, and chimeric or human, humanized, neutralizing, bispecific or single chain antibodies thereof. Antibodies of the present invention can have additional moieties attached thereto.

Antibody or antibody-like molecules of the instant invention can be administered as a component of a pharmaceutical composition or medicament. Pharmaceutical compositions or medicaments generally contain the active therapeutic agent and a variety of other pharmaceutically acceptable components.

Hybrid Antibodies and Fusion Proteins

An antibody fusion protein can also be made using the altered constant region of the IgG as proposed in this invention. The antigen binding regions of the antibody for example, Fab, F(ab)2, SCFv can be fused with the CH2-CH3 with or without the linker. Additional linkers known in the art can also be used. Fusion proteins in which CH2 is replaced with CH1 are also described herein. The CH1 region is benign and does not cause the undesired Fc effector functions. Due to the FcRn binding region in the CH3 domain the half life of the molecule will remain similar to the molecule with both CH2 and CH3 at their original positions. Antibodies with deleted CH1 and CH2 regions have also been made and produced. The present invention covers the following antibodies:

1) Aglycosylated IgG2 and IgG4 antibodies. Aglycosylation is produced as a result of mutation at the 297 position.

2) Aglycosylated IgG2 containing H268Q, V309L, A330S, and P331S mutations to reduce the effector functions beyond the baseline set for an aglycosylated IgG2.

3) Aglycosylated IgG1 and IgG4 hybrids where CH1 is from an IgG1 or IgG3 and CH2 and CH3 is from and IgG2 or IgG4. The 297 residue in IgG4 is mutated from N297 to A297.

4) Antibodies wherein the CH2 domain is replaced with CH1 domain making the construct to be F(ab)2-CH1-CH3.

In 4), a linker is added between the Fab and the CH1 and between CH1 and CH2. The final construct would have one of the following (or similar) structures; a) Fv-CH1-Linker-CH1-Linker-CH3 orb) Fv-CH1-linker-CH2-linker-CH3. CH1 is a non activating constant region and therefore was used to generate the elongated Fab with longer half life. The linker can be of various types especially those known in the art, such as (GGGGS)n (SEQ ID NO: 1). Fusion proteins and/or antigen binding fragments, or any receptor protein polypeptides, can be mounted onto CH2-CH3 via any linker known in the art, such as those (GGGGS)n (SEQ ID NO: 1). Various modifications and combinations can be made from structures a) and b) such as varying the position of the linkers between the Fv, CH1, CH2 and CH3. The presence and absence of linkers can create molecules of interest with longer half life. An Fc fusion combines the Fc region of an antibody, and thus its favorable effector functions and pharmacokinetics, with the target-binding region of a receptor, ligand, or some other protein or protein domain. Due to the functional overlap of Fc fusions with antibodies, the present invention includes the Fc fusions.

For an AP neutralizing antibody in particular it is crucial that the mediated Fc response be minimized and that C1q binding is inhibited. Our goal is to generate, as an alternative to complete removal of the Fc region, therapeutic AP neutralizing antibodies with reduced Fc and C1q binding. Numerous reports have now shown that single or multiple point mutations within the Fc region (CH2 and CH3 domains) can reduce binding of the antibody to Fc receptors and to C1q—thereby reducing the undesired effector functions without compromising the antibody's serum life. Antibodies with such modifications are useful in the development of any therapeutic antibody targeting the AP, which is intended to neutralize the AP without activating the CP (via effector functions). Aglycosylation of IgG2 has never been described for the purpose of preventing CP activation and other Fc effector functions of the antibody. This is an innovation of the present invention.

Example 1

Binding Affinity to the Target Protein Properdin

The wild type IgG2, aglycosylated IgG2, and aglycosylated IgG1/IgG2 Hybrid antibodies bind the target protein with high affinity. In a typical assay, polystyrene microtiter plates were coated with human factor P, (Complement Technologies, San Diego, Calif.) in phosphate buffered saline (PBS) overnight. After aspirating the factor P solution, wells were blocked with PBS containing 1% bovine serum albumin (BSA) (Sigma Chemical Company, St. Louis, Mo.) for 2 hours at room temperature. Wells without factor P coating served as background controls. Aliquots of various concentrations of the antibodies under investigation in blocking solutions were added to factor P-coated wells and plates were allowed to sit for 1 hour to allow the monoclonal antibodies to bind the substrate-bound factor P. The plate was rinsed with PBS and factor P-bound monoclonal antibodies were detected by the addition of peroxidase-conjugated goat anti-human monoclonal antibody (detection antibody) (American Qualex) at 1:2000 dilution in blocking solution, which was allowed to incubate for 1 hour at room temperature. After washing the plates with PBS, 100 µl of 3,3',5,5'-tetramethyl benzidine (TMB) substrate (Kirkegaard & Perry Laboratories, Gaithersburg, Md., Cat. No. A50-65-00) was added. After incubation for 10 minutes at 25° C., the reaction of TMB was quenched by the addition of 100 µl of phosphoric acid, and the plate was read at 450 nm in a microplate reader (e.g., SPECTRA MAX® 250, Molecular Devices, Sunnyvale, Calif.).

Figure 4:
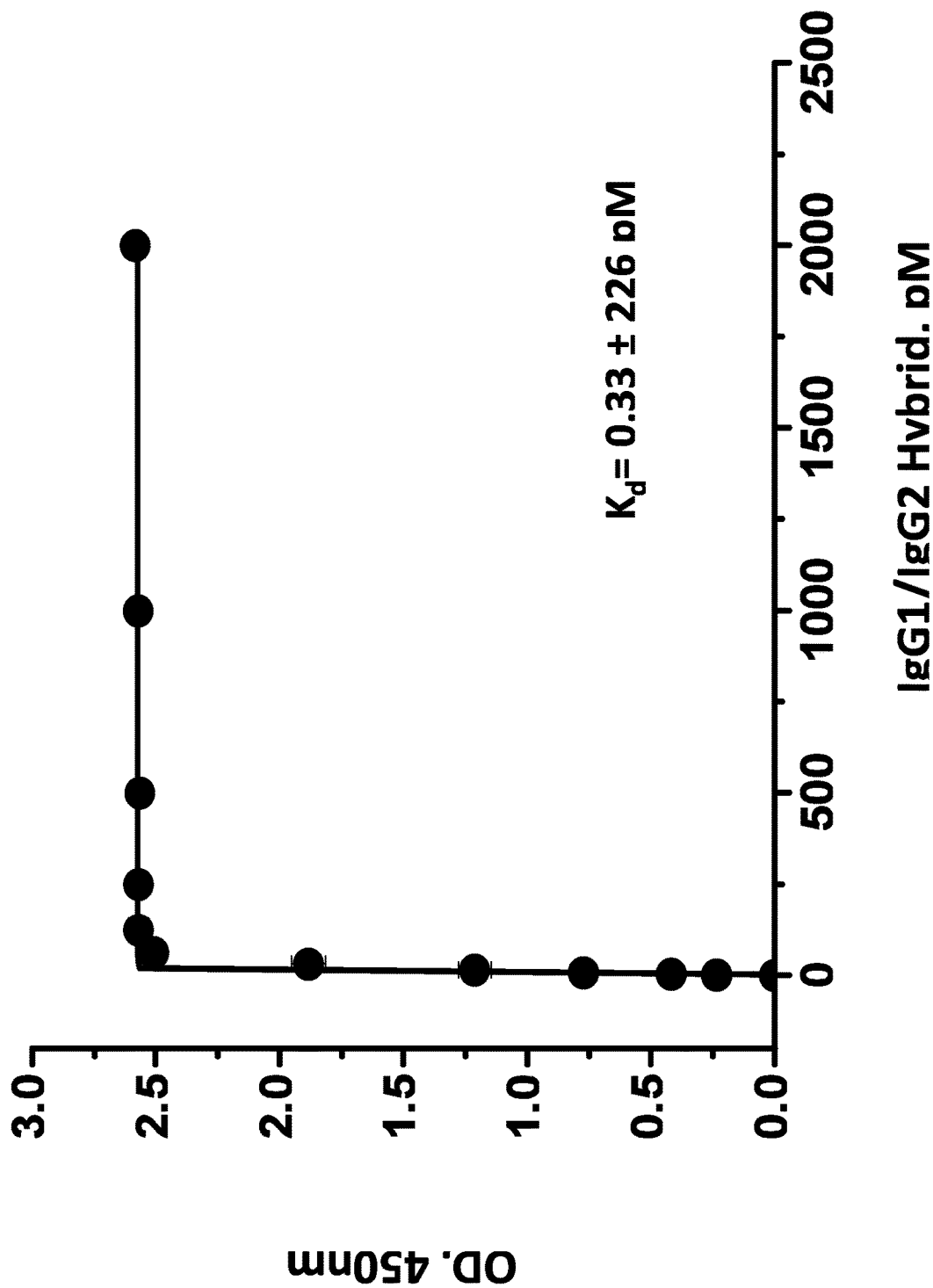
FIG. 4. Depicts binding of an aglycosylated IgG2 (297 mutation) hybrid of an IgG1 and IgG2 to substrate bound antigen. The aglycosylated hybrid antibody binds its target antigen with high affinity.
Figure 5:
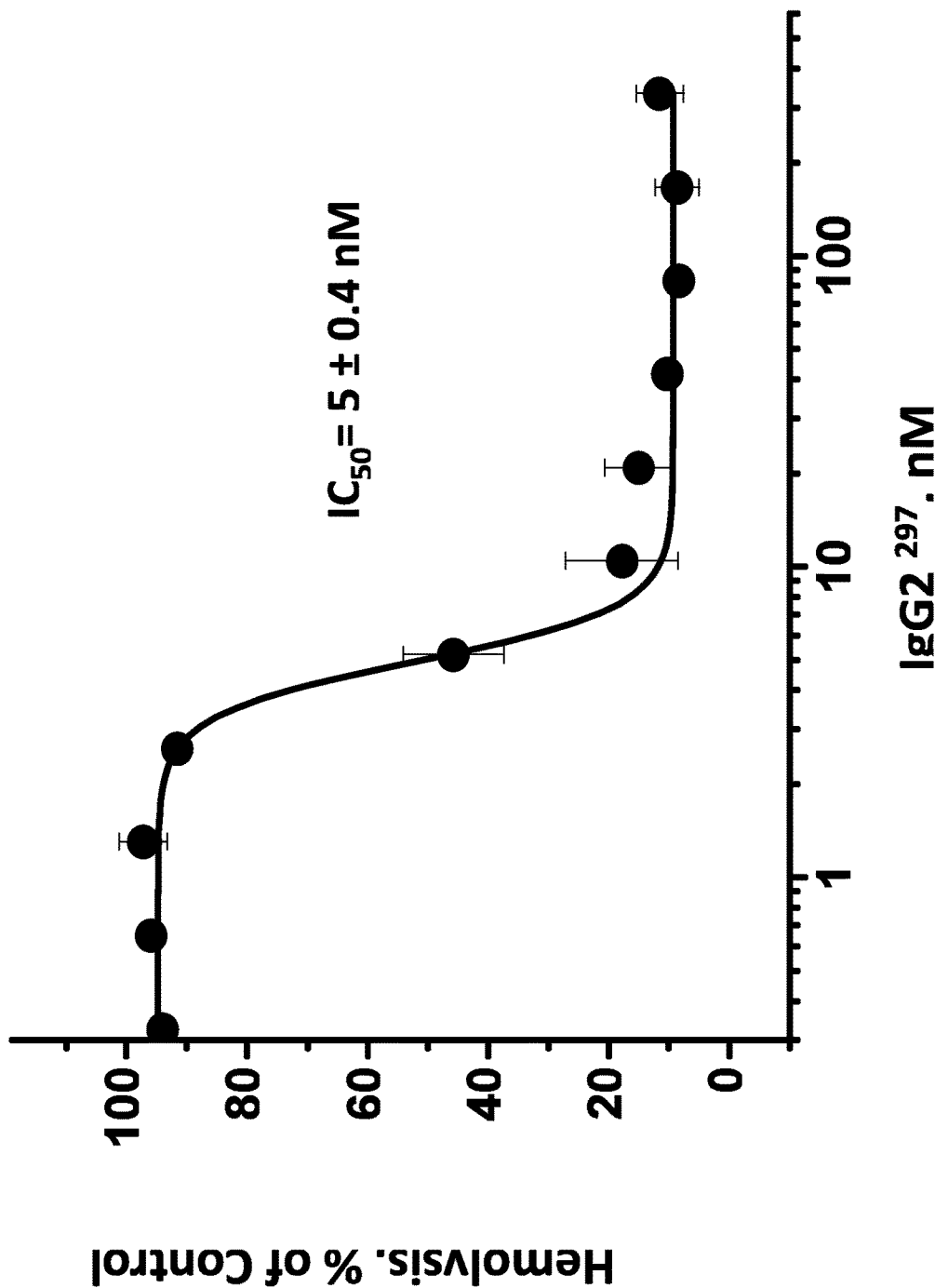
FIG. 5. Depicts the inhibition of alternative pathway by an IgG2 (297 mutation) in normal human serum. The aglycosylated hybrid antibody binds and neutralizes an alternative pathway specific protein.
Figure 11:
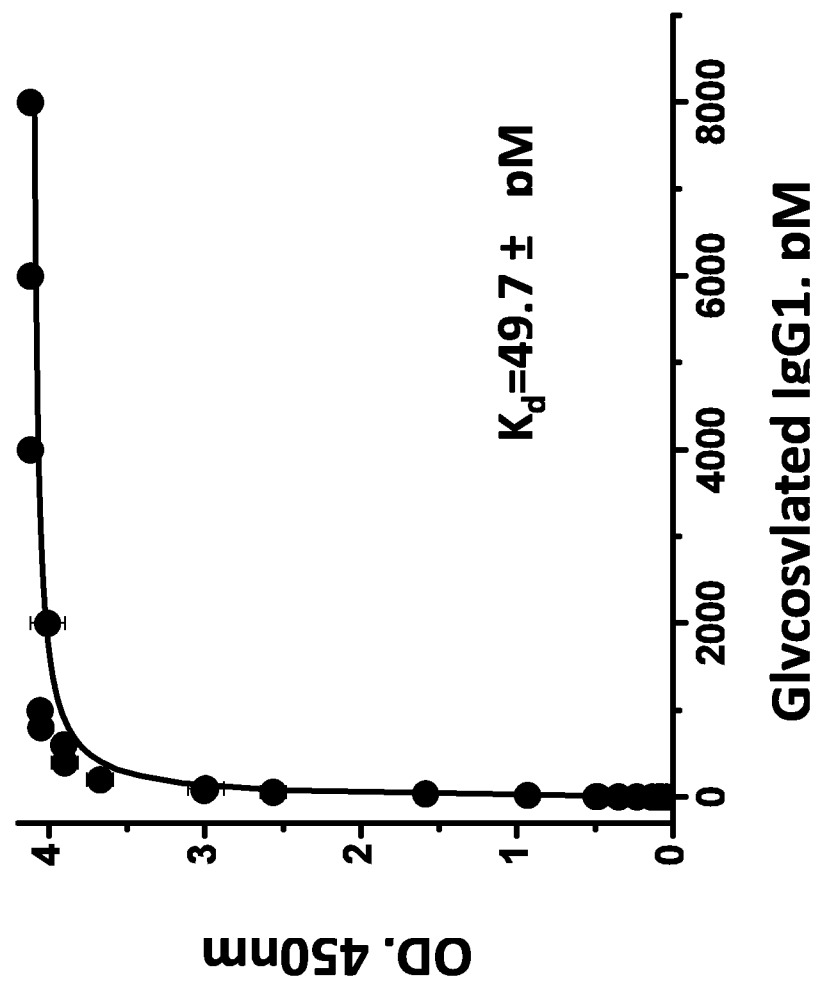
FIG. 11. Demonstrates that glycosylated IgG1 antibody binds target antigen properdin with high affinity.
Figure 12:
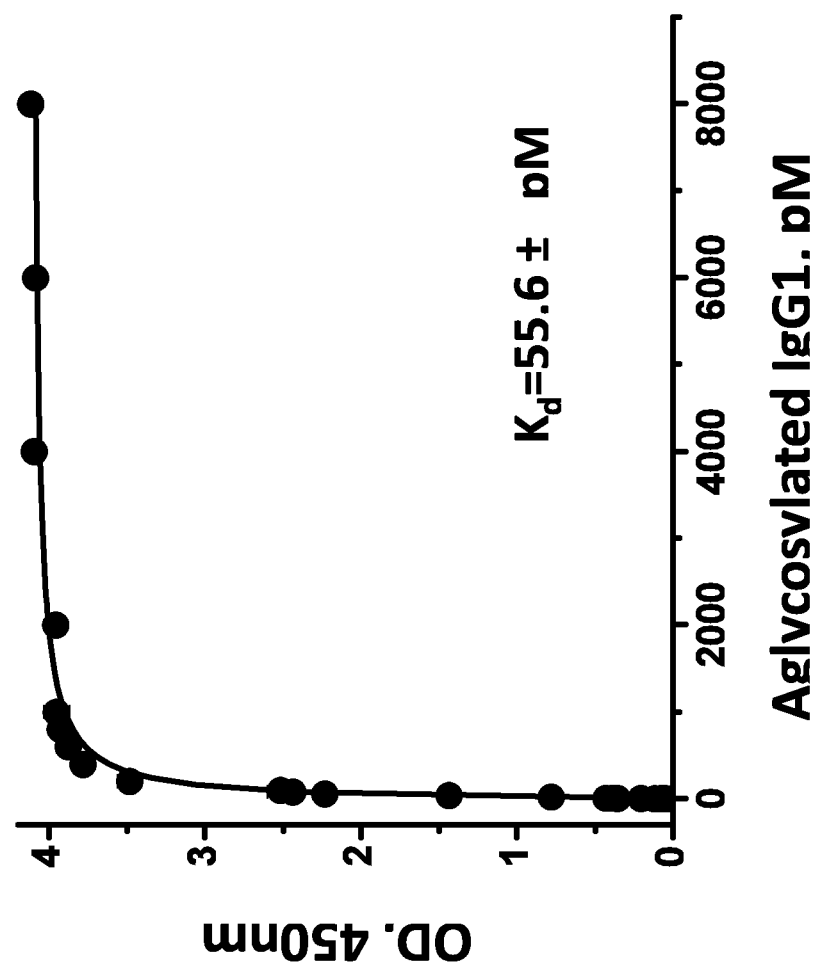
FIG. 12. Demonstrates that aglycosylated IgG1 (297 mutation) antibody binds the target protein properdin with high affinity.

All three types of IgG2 antibodies, IgG2 wild type, IgG2 with 297 mutation, and IgG1/IgG2 hybrid with 297 mutation, bind the target protein with high affinity as shown in FIGS. 2, 3, and 4, respectively. As shown in As shown in FIGS. 11 and 12, both glycosylated IgG1 and aglycosylated IgG1 with 297 mutation bind the target protein properdin with low picomolar affinity.

Example 2

Bioassay to Demonstrate Inhibition of Alternative Pathway Activation (AP)

To assess the ability of the exemplary compounds of the present invention to inhibit AP activation in an in vivo-like system, an erythrocyte hemolysis assay was used. Rabbit red blood cells (rRBCs) were incubated with normal human serum (NHS) in an AP enabling buffer. The presence of rRBCs ("the foreign body") preferentially induces activation of the AP, resulting in C5b-9 deposition on the erythrocytes and ultimately causing cell lysis. The extent of cell lysis is detected based on light scattering at optical density of 700 nm.

Introducing rabbit Erythrocytes (rRBC) into 10% human serum (with $Mg^{2+}$/EGTA) represents the introduction of a foreign cell surface which initiates the alternative complement cascade. Activation of the AP results in the formation of MAC which causes lysis of the foreign cells (the rRBCs). The selected antibodies of the present invention prevent lysis of these erythrocytes. This process was quantified after examining the light scattering caused by intact red blood cells.

Figure 6:
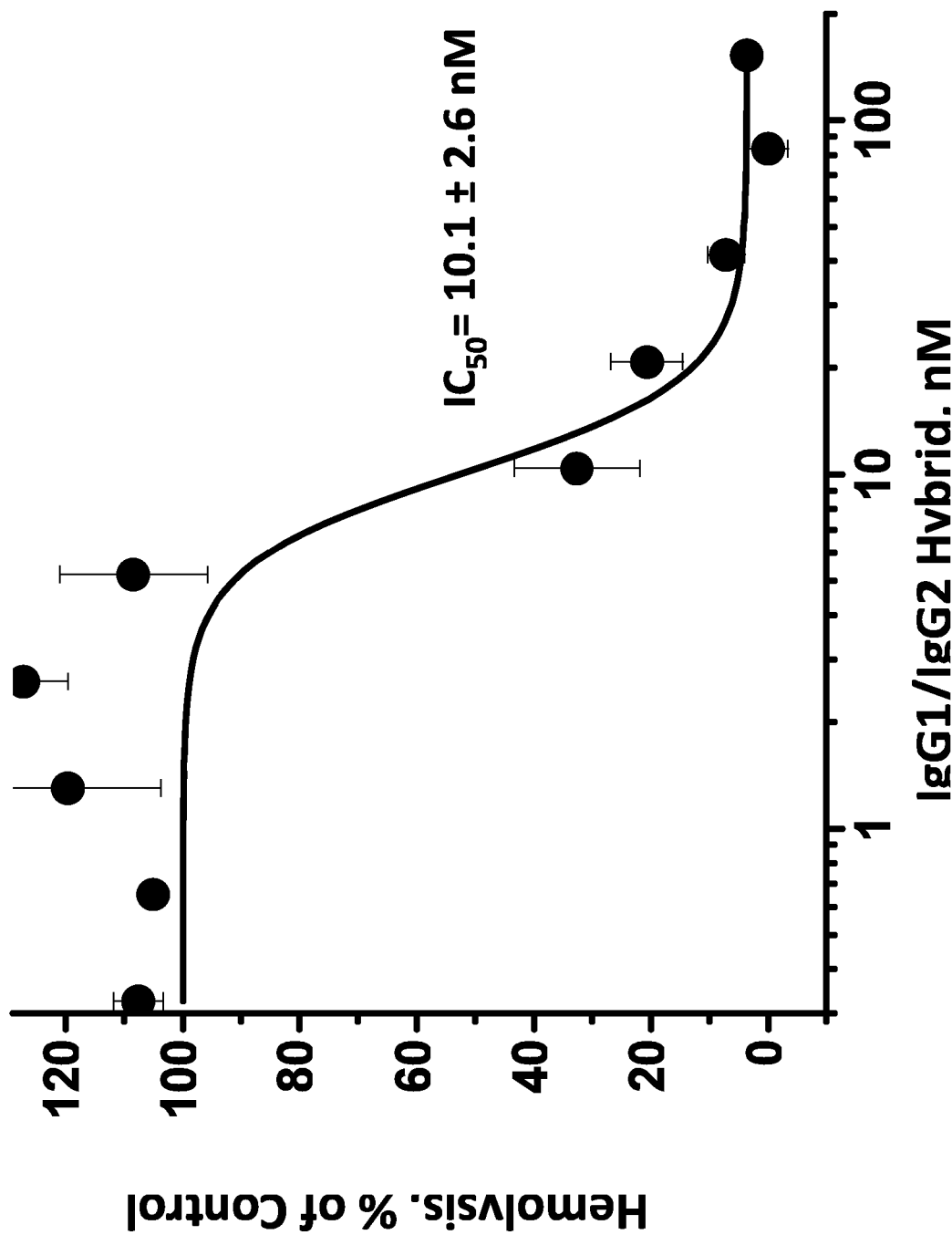
FIG. 6. Depicts the inhibition of alternative pathway by an IgG1/IgG2 Hybrid with 297 mutation in normal human serum. The hybrid antibody binds and neutralizes the alternative pathway specific protein.
Figure 7:
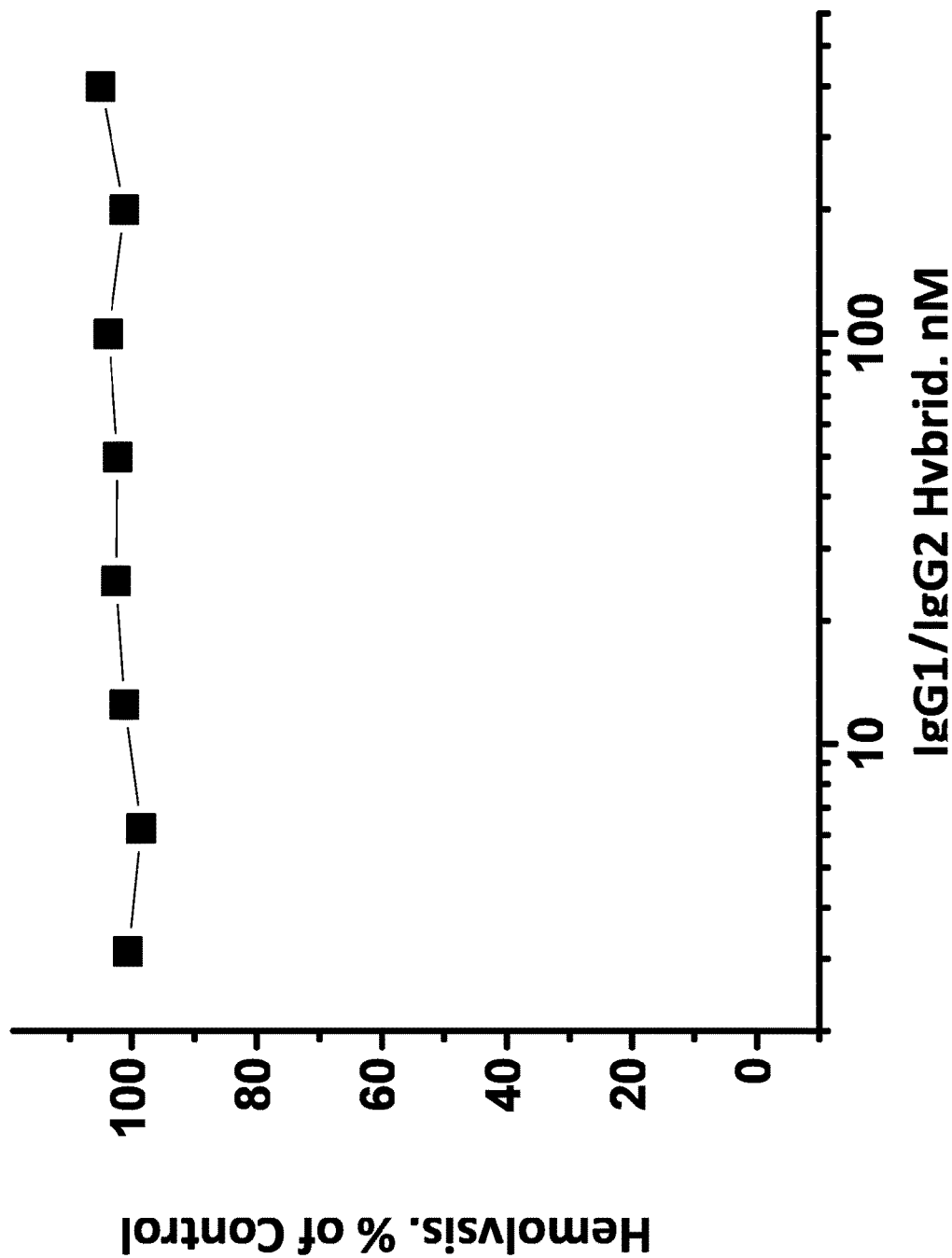
FIG. 7. Depicts the lack of inhibition or activation of the classical pathway by an IgG1/IgG2 Hybrid with 297 mutation in normal human serum. The hybrid antibody does not affect the activity of the classical pathway.
Figure 8:
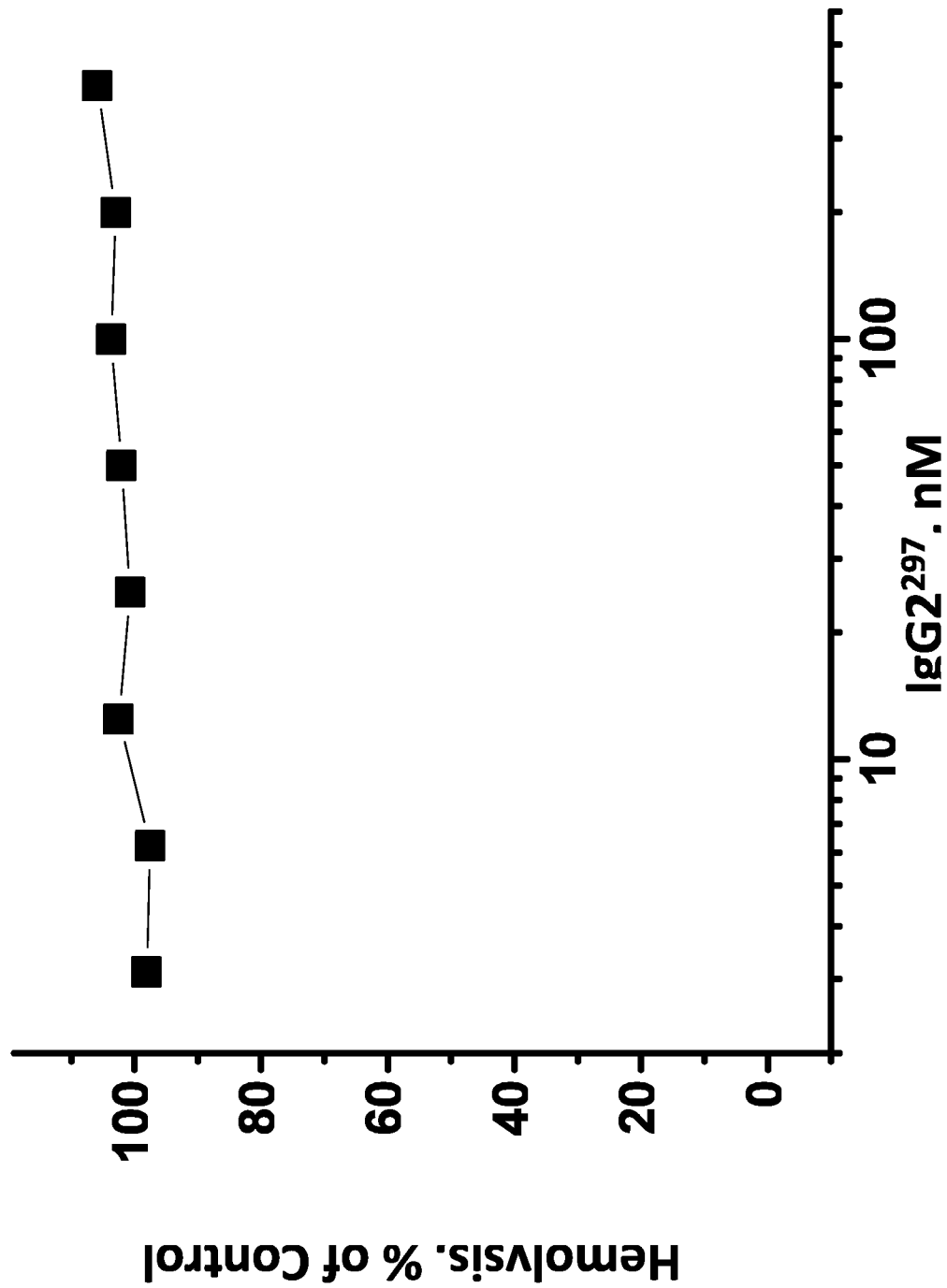
FIG. 8. Depicts the lack of inhibition or activation of the classical pathway by antibody with an IgG2 Fc region with 297 mutation in normal human serum. The aglycosylated IgG2 antibody binds and does not affect the activity of the classical pathway.
Figure 9:
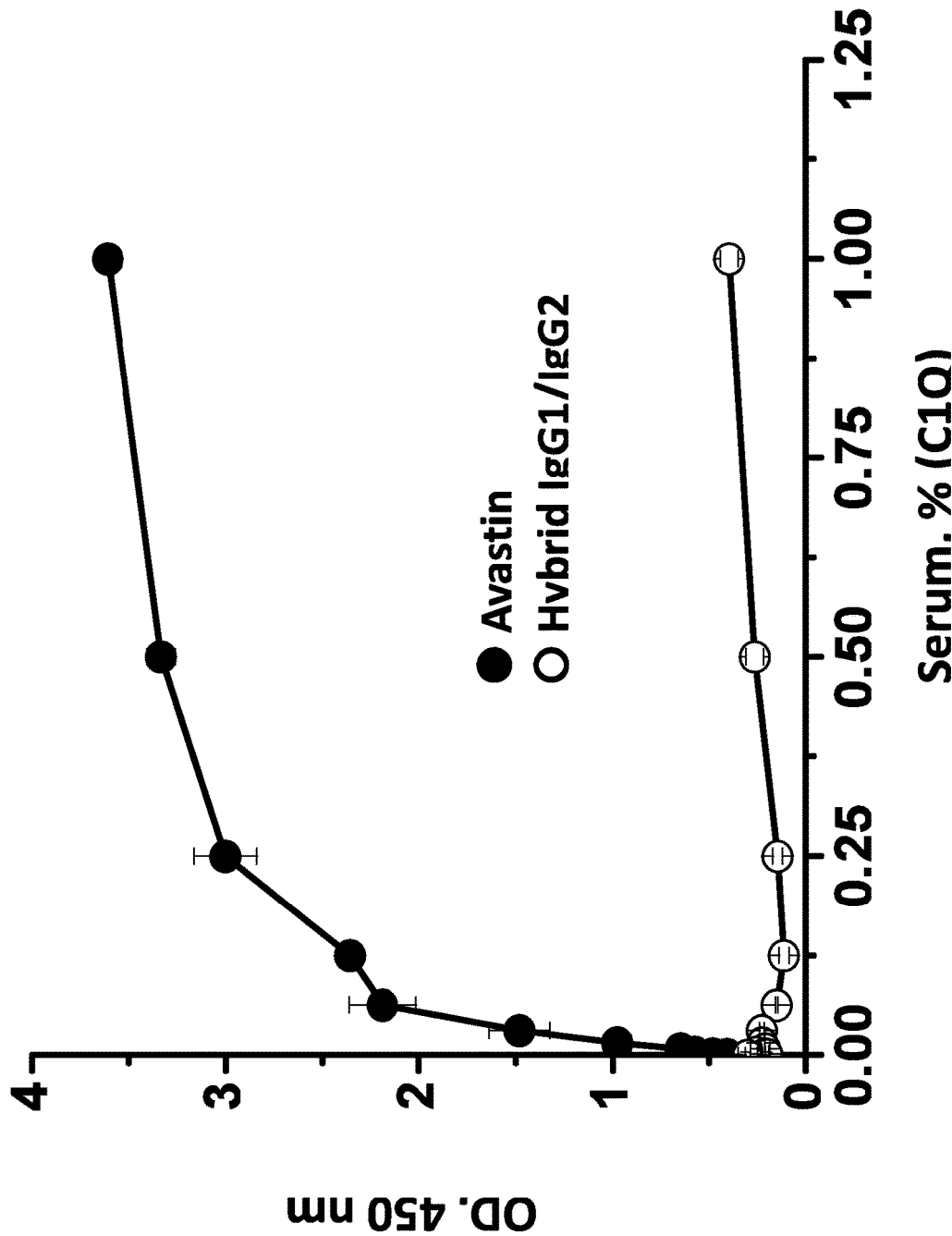
FIG. 9. Demonstrates that the IgG1/IgG2 Hybrid antibody does not bind C1q in normal human serum. C1q was used as a source of C1q. Avastin® antibody was used as positive control which binds C1q with high affinity.
Figure 10:
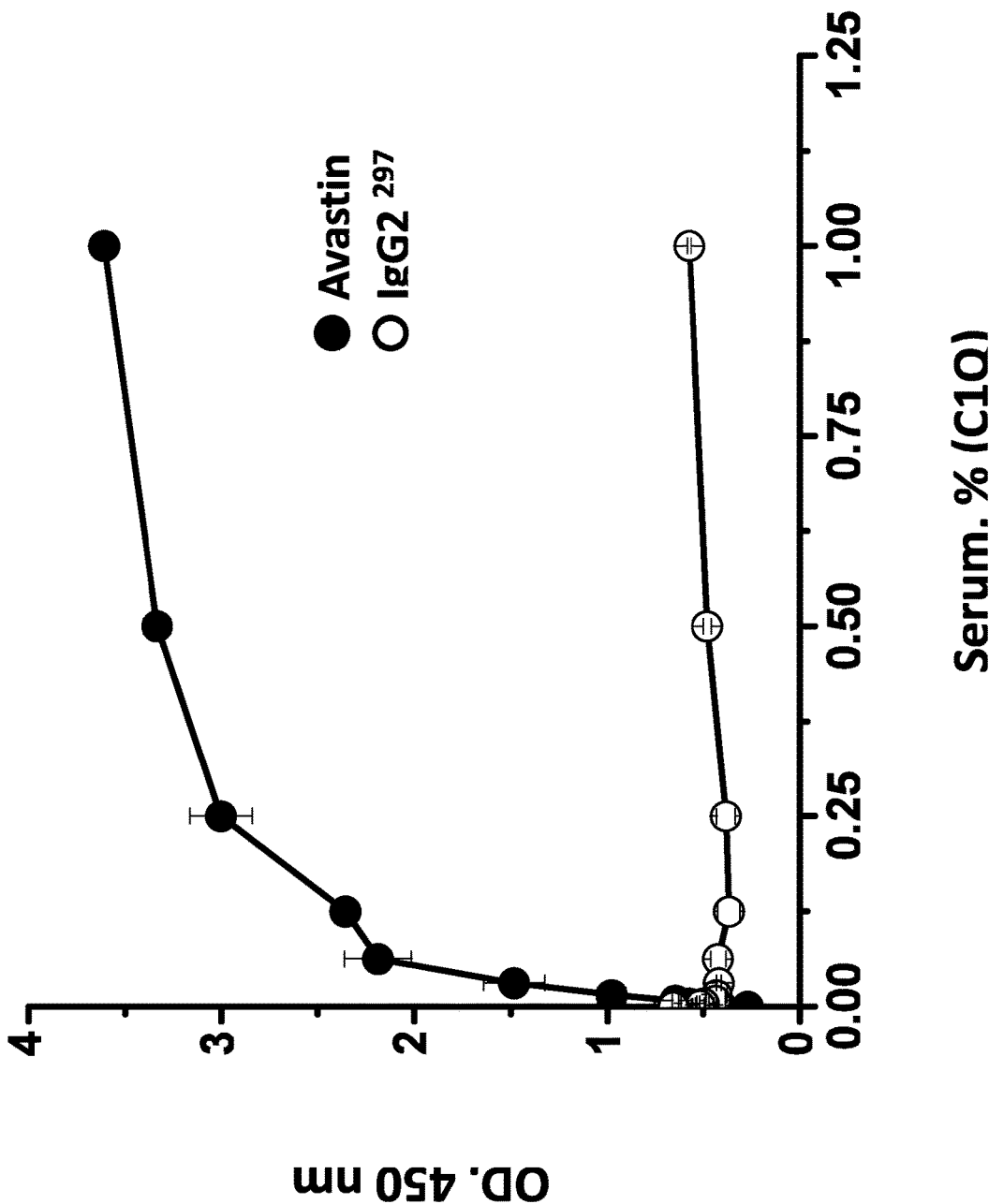
FIG. 10. Demonstrates that aglycosylated IgG2 (297 mutation) antibody does not bind C1q in normal human serum. Human Serum was used as a source of C1q. Avastin® antibody was used as positive control which binds C1q with high affinity.
Figure 13:
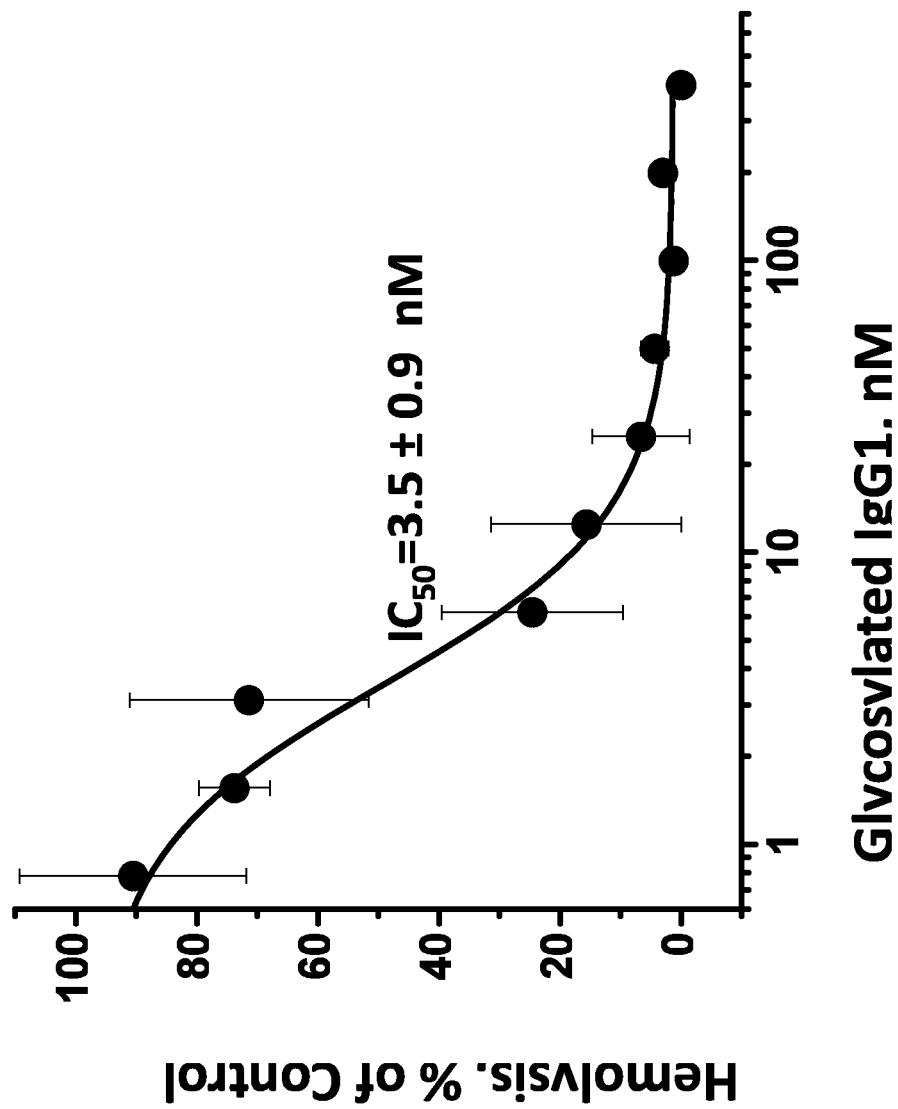
FIG. 13. Demonstrates that glycosylated IgG1 antibody inhibits AP activation.
Figure 14:
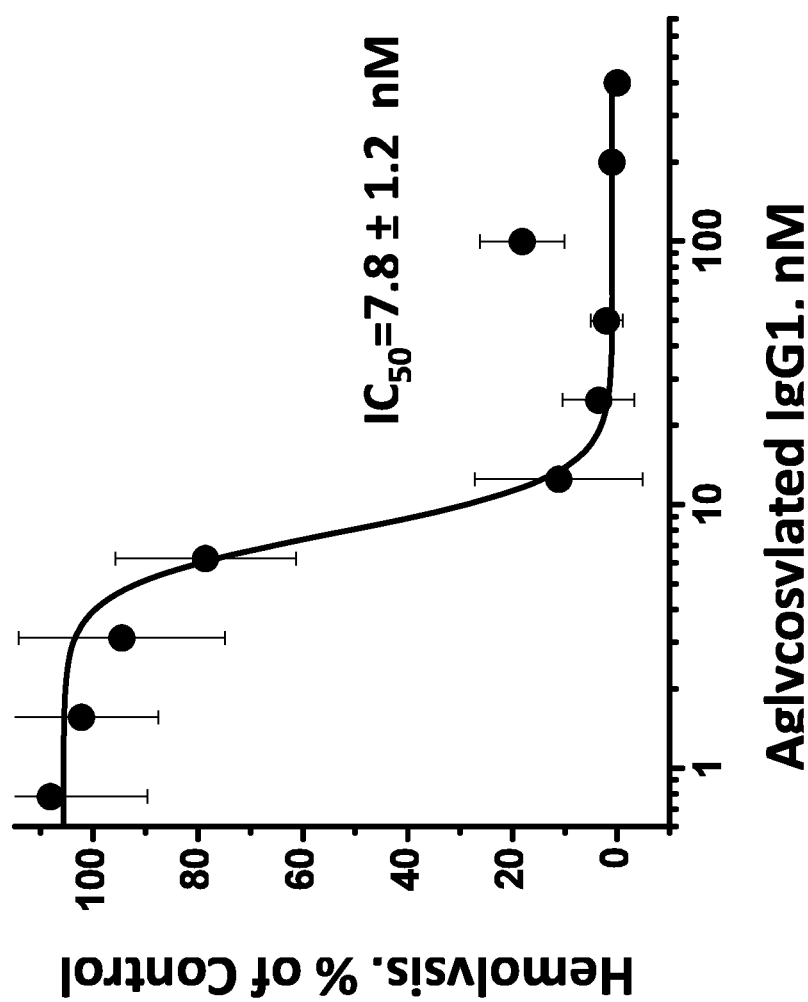
FIG. 14. Demonstrates that aglycosylated IgG1 (297 mutation) antibody inhibits AP activation FIG. 15. Demonstrates that aglycosylated IgG1 (297 mutation) antibody does not bind C1q in normal human serum. Glycosylated antibodies bind the C1q.

It is well established that rabbit erythrocytes specifically activate the AP, with a resulting lysis of the rRBCs by the C5b-9 (MAC) complex. A progressive decrease in light scatter (due to lysis of intact cells) was measured at 700 nm as a function of time in a temperature-controlled ELISA plate reader. The data were recorded and analyzed with a Spectramax® 190 plate reader and SoftMax® Pro software. The results were plotted with MicroCal® Origin Software. As shown in FIGS. 6 & 7, both aglycosylated (IgG2 with 297 mutation) and aglycosylated hybrid antibody (IgG1/IgG2 with 297 mutation) inhibit AP activation. As shown in FIGS. 13 and 14, glycosylated IgG1 and aglycosylated IgG1 with 297 mutation inhibit the alternative pathway activation with similar efficacy.

Example 3

The Aglycosylated Antibodies do not Inhibit or Activate the Classical Pathway

IgG2 (unaltered) is known to activate the complement pathway according to the known literature—see FIG. 1. To test the effects of the antibody on the CP, antibody-sensitized, sheep erythrocytes (sRBC) were incubated in 1% normal human serum in CP buffer ($Ca^{2+}$/$Mg^{2+}$). These sRBCs activate the CP, which induces lysis of cell membranes. Lysis of the cell membranes results in a gradual decrease in light scattered by cells. When an alternative pathway specific antibody of the present invention was incubated with sRBCs at 37° C. in 1% NHS with a buffer containing $Ca^{2+}$ and $Mg^{2+}$ ("the CP buffer") no effect on hemolysis was observed within the time period beginning with the start of hemolysis and concluding with maximal hemolysis. This implies that the alternative pathway neutralizing IgG2 antibody does not affect CP hemolytic activity in NHS (data not shown). Light scatter (due to lysis of intact cells) was measured at 700 nm as a function of time. The activation of the classical pathway did not rise above the 100% control levels, suggesting that neither aglycosylated antibody nor the aglycosylated hybrid IgG1/IgG2 antibody activates the classical pathway. In contrast, the IgG1 by itself is known to activate the classical pathway.

Example 4

Binding Affinity to Complement C1q

C1q binding to the antibody begins classical complement pathway activation as an effector function of the antibody. The degree of C1q binding varies with the type of antibody and is found to be greater for an IgG1 isotype compared to an IgG2 isotype. Complement Dependent Cytotoxicity (CDC) is also mediated via C1q binding. Thus, the more the antibody binds to C1q, the higher the CP activation and CDC activity. Likewise, a lack of C1q binding is directly correlated to the lack of CDC activity. The binding of all antibodies in question was evaluated using a binding assay. A medium binding 96-well plates were coated overnight at 4° C. with 2 µg/mL of antibodies in PBS. The plates were washed after each incubation step with phosphate buffered saline, pH 7.4, and incubations were performed at room temperature. After coating, the plates were blocked with 200 µL/well of blocking solution (1% BSA in PBS) for 1 hour, and incubated for 1 hour with various concentrations of normal human serum that contains endogenous levels of C1q. Following incubation and washing, the bound C1q was detected an HRP conjugated Goat anti-human C1q antibody (Complement Technology, Tyler, Tex.) and TMB as substrate (Kirkegaard & Perry). The reaction was stopped by adding 100 µL of 1 M $H_2SO_4$ solution. The final signal was measured by absorbance at 450 nm (Spectramax® 190 and 250 plate reader).

Figure 15:
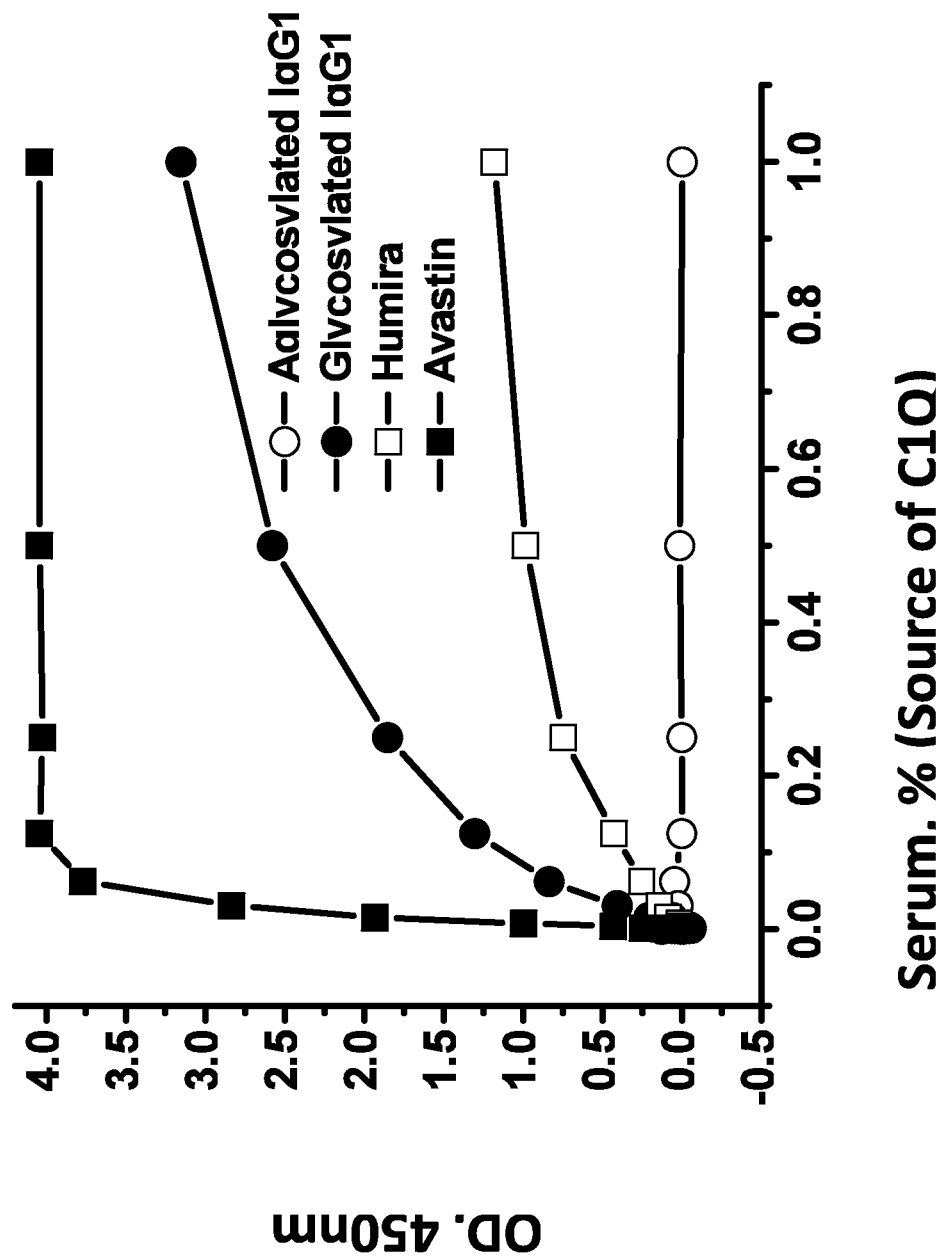

As shown in FIG. 15, Avastin® antibody binds very strongly to C1q, due to the fact that Avastin® antibody's Fc domain was designed to bind C1q with enhanced CDC activity. Humira® antibody also demonstrated significant C1q binding. Humira® antibody's Fc region was unaltered. The glycosylated IgG1 also demonstrated binding to C1q. However, the aglycosylated IgG1 does not bind C1q and therefore would not exhibit CDC activity.

Example 5

Binding Affinity to Fc.Gamma.RI and Fc.Gamma.RIII Proteins

Figure 16:
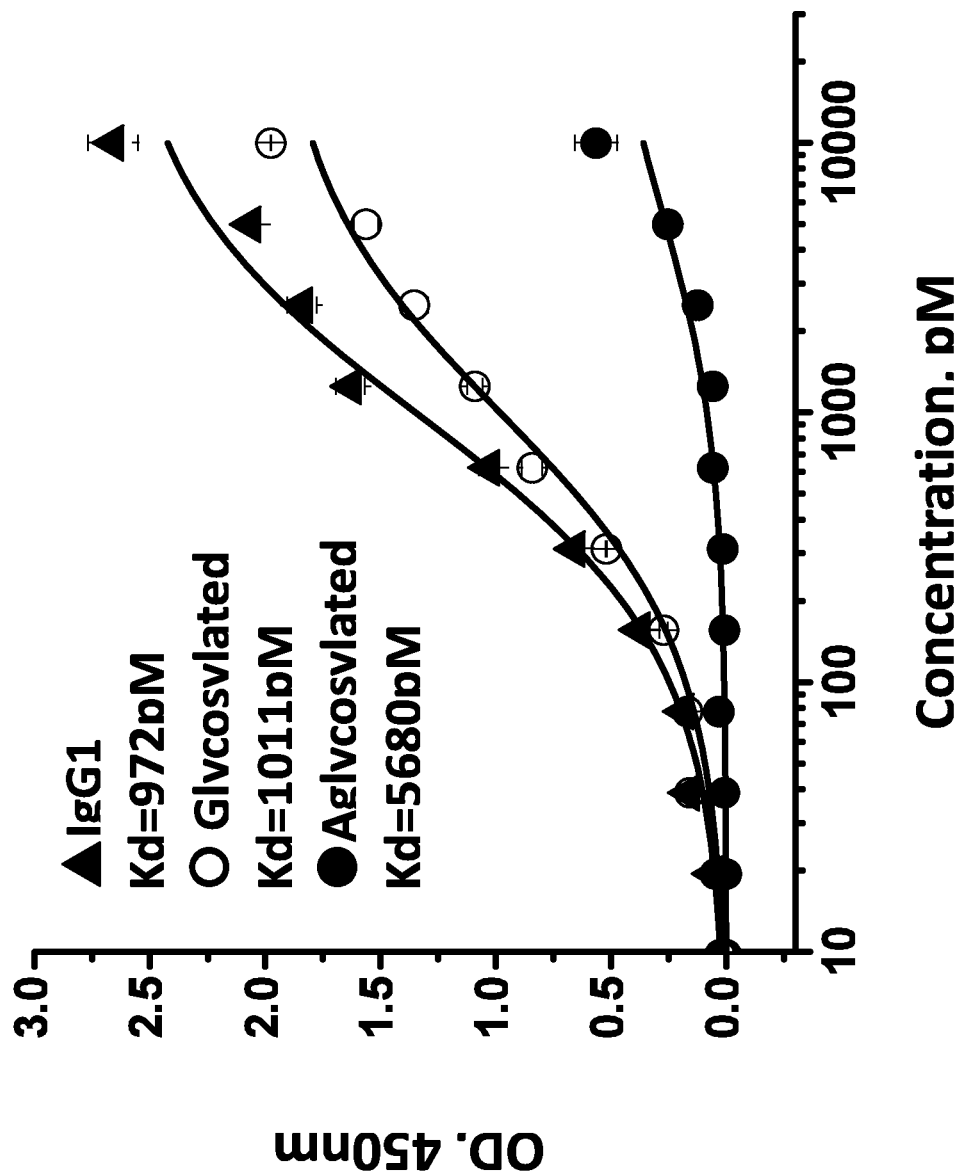
FIG. 16. Demonstrates that aglycosylated IgG1 (297 mutation) does not bind the Fc.gamma.RI protein FIG. 17. Demonstrates that aglycosylated IgG1 (297 mutation) antibody does not bind Fc.gamma.RIII protein.

Fc effector functions are important for cellular functions and cell activation. For therapeutic antibodies, it is important that these antibodies do not cause cellular activation and antibody mediated cellular toxicity. IgG1 isotype is known to display activation of FcγRI receptors with high binding affinity. The binding affinity of this particular isotype to FcγRII and RIII is lower than to FcγRI. IgG2 isotypes typically display low binding affinity to these Fc gamma receptors, as shown in FIG. 1. By making aglycosylated isoforms of IgG1 and IgG2, ADCC activity can be lowered further. FIG. 16 shows that aglycosylated IgG1 shows lack of binding to FcγRI and FcγRIII receptors tested. Medium binding 96-well plates from Costar were coated overnight at 4° C. with Fc gamma peptides. The plates were washed after each incubation step with phosphate buffered saline, pH 7.4, and incubations were performed at room temperature. After coating, the plates were blocked with 200 µL/well of blocking solution (1% BSA in PBS) for 1 hour, and incubated for 1 hour with various concentrations of antibodies in blocking solution. Following incubation and washing, the bound antibody was detected an HRP conjugated Goat anti-human IgG antibody (Complement Technology, Tyler, Tex.) and TMB as substrate (Kirkegaard & Perry). The reaction was stopped by adding 100 µL of 1 M $H_2SO_4$ solution. The final signal was measured by absorbance at 450 nm (Spectramax® 190 and 250 plate reader).

Figure 17:
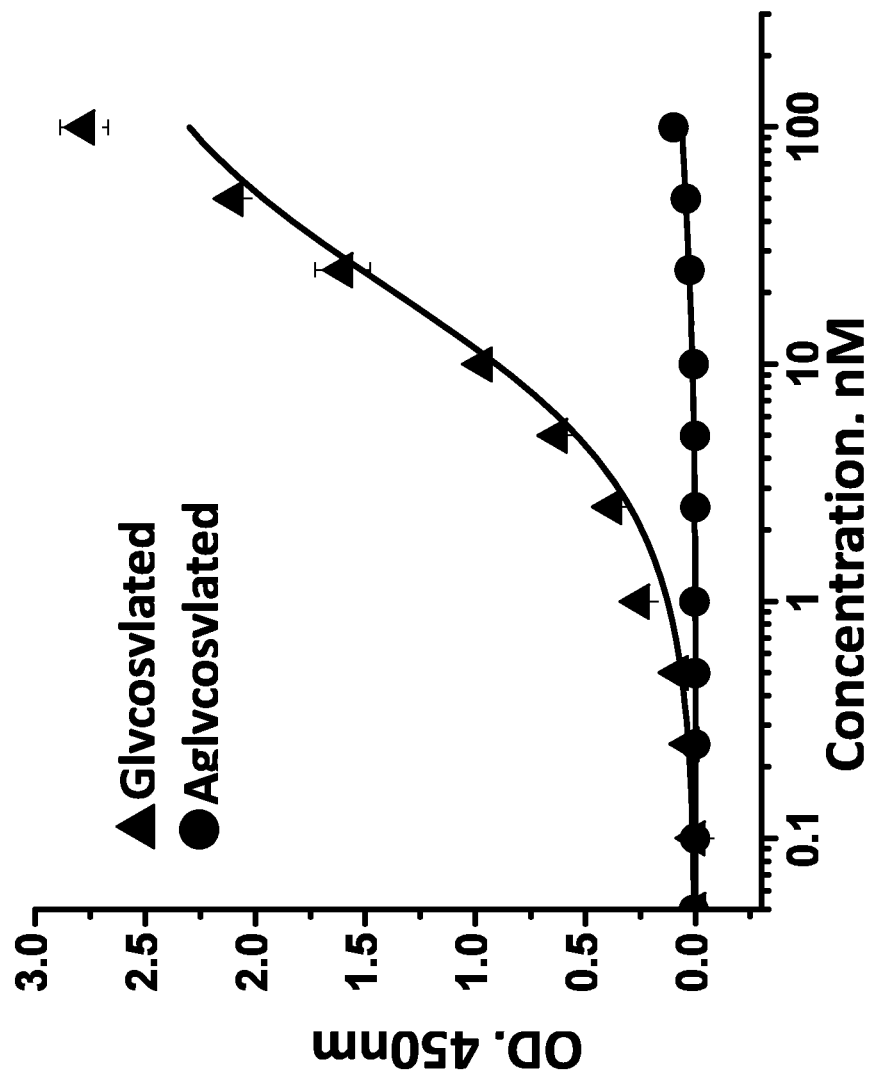

As shown in FIGS. 16 and 17, aglycosylated antibody does not show binding to the Fc receptors.

The invention claimed is:

1. A method for reducing antibody-mediated classical complement pathway activation, comprising administering to a subject an engineered form of a parent antibody which binds to properdin, the engineered antibody contains a human heavy chain IgG1 CH1 portion and a human IgG2 Fc portion, wherein the engineered antibody comprises a substitution at position 297 from asparagine (N) to Alanine (A) or Glutamine (Q) in the CH2 region of said heavy chain constant region that prevents glycosylation of the substitution position.

2. The method of claim 1, wherein the engineered antibody comprises a variable region derived from the parent antibody of IgG1, IgG2, IgG3, or IgG4 isotype.

3. The method of claim 2, wherein the variable region is derived from the parent antibody of IgG1 or IgG2 isotype.

4. The method of claim 2, wherein a variable region is from the parent antibody of IgG1 isotype.

5. The method of claim 1 wherein the engineered antibody has reduced ADCC and CDC activity compared to the parent antibody.

6. The method of claim 5, wherein the parent antibody is an IgG1 antibody or IgG2 antibody.

7. The method of claim 1, further comprising engineering the parent antibody substituting the Fc region of the parent antibody with a human IgG2 Fc portion having a substitution at position 297 from asparagine (N) to Alanine (A) or Glutamine (Q) in the CH2 region, wherein the parent antibody is an IgG1 or IgG2 antibody.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Gly Gly Gly Gly Ser
1               5
```